(12) United States Patent
Butty et al.

(10) Patent No.: US 6,346,422 B1
(45) Date of Patent: Feb. 12, 2002

(54) METHOD OF SELECTING BACTERIAL STRAINS

(75) Inventors: Pascal Jean-Luc Butty, Montpellier (FR); Marina Jeyasingham, Aberdeen (GB)

(73) Assignee: Ceva Sante Animale, Libourne (FR)

( * ) Notice: Subject to any disclaimer, the term of this patent is extended or adjusted under 35 U.S.C. 154(b) by 0 days.

(21) Appl. No.: 09/301,559

(22) Filed: Apr. 29, 1999

(30) Foreign Application Priority Data

Apr. 30, 1998 (FR) .......................................... 98 05559

(51) Int. Cl.$^7$ ....................... G01N 33/567; A01N 63/00
(52) U.S. Cl. .................. 436/503; 435/7.32; 435/252.4; 435/7.1; 424/93.48
(58) Field of Search ........................... 424/93.1, 93.45; 435/7.1, 7.32, 7.37, 252.4; 800/2; 530/300; 436/503

(56) References Cited

U.S. PATENT DOCUMENTS

| | | | | |
|---|---|---|---|---|
| 5,164,298 A | * | 11/1992 | Lingwood | 435/7.37 |
| 5,206,015 A | * | 4/1993 | Cox et al. | 424/93 |
| 5,308,615 A | * | 5/1994 | Deloach et al. | 424/93 |
| 5,401,501 A | * | 3/1995 | Pratt | 424/93.5 |
| 5,413,785 A | * | 5/1995 | Nanji | 424/93.45 |
| 5,604,127 A | * | 2/1997 | Nisbet et al. | 435/252.4 |
| 5,625,124 A | * | 4/1997 | Falk et al. | 800/2 |
| 5,773,000 A | * | 6/1998 | Bostwick et al. | 424/167.1 |
| 5,968,569 A | * | 10/1999 | Cavadini et al. | 426/61 |
| 6,010,695 A | * | 1/2000 | Line et al. | 424/93.1 |
| 6,040,421 A | * | 3/2000 | Tarr et al. | 530/300 |
| 6,100,388 A | * | 8/2000 | Casas et al. | 536/23.5 |

FOREIGN PATENT DOCUMENTS

| WO | WO 97/14802 | | 4/1997 | |
|---|---|---|---|---|
| WO | 97/20577 | * | 6/1997 | A61K/39/395 |

OTHER PUBLICATIONS

Soderlind, et al, Infection Immunity, vol. 36,(3) pp. 900–906, Jun. 1982.*
Evans, DG et al, Infection Immunity, vol. 18(2), pp. 330–337, Nov. 1977.*
McKee, ML et al, Infection Immunity, vol. 63(9), pp. 3739–3744, Sep. 1995.*
Newburg, D.S et al, J. Infectious Disease, Fol. 166, pp. 832–836, 1995.*
Rikitomi, N et al, Kansenshogaku Zasski, vol. 63(2), pp. 118–224, (abstract), Feb. 1989.*
Chan, RC et al, J. Urol., Mar. 1984, vol. 131(3), pp. 596–601, (abstract).*
Schoeni, JL et al, Applied Environmental Microbiology, vol. 60(4), pp. 1191–1197, (abstract), 1994.*
Durant, JA et al, Int. J. Food Microbiology, vol. 38(2–3), pp. 181–189, (abstract), Sep. 1997.*
Promsopone, B et al, J. Food Prot. vol. 61(2), pp. 176–180, (abstract), Feb. 1998.*
Lodinova–Zadnikova et al, Vet. Q. vol. 20(suppl. 3), pp. S78–S81, (abstract), Jun. 1998.*
Fukushima, Y et al, Int. J. Food Microbiol., vol. 42 (1–2), pp. 39–44,(abstract), 1998.*
Morishita, TY et al, Avian Dis, vol. 41(4), pp. 850–855, (abstract), Dec. 1997.*
Wagner, RD et al, Infection Immunity, vol. 65(8), pp. 3345–3351, (abstract), Aug. 1997.*
Nemcova, R., Vet. Med. vol. 42(1), p. 19–27, (abstract), Jan. 1997.*
Lykova, EA et al, AH Mikrobiol Epidemiol Immunobiol, Mar.–Apr., vol. 2, pp. 88–91 (abstract), 1996.*
Blomberg, L et al, Applied and Environmental Microbiology, vol. 59(1), pp. 34–39, Jan. 1993.*
Yamamoto, K et al, Biochemical and Biophysical Research Communications, vol. 228, pp. 148–152, 1996, Binding specificities of Lactobacillus to Glycolipids.*
Biological Abstracts, vol. 89, Abstract No. 105607: Valpotic et al, "Phenotyping of pigs for the presence of intestinal receptors mediating adhesion of enterotoxigenic *Escherichia coli* bearing K88AC pilus antigen by ELISA", Veterinarski Archiv vol. 59, No. 4, 1989, pp. 161–175.

* cited by examiner

*Primary Examiner*—Lynette R. F. Smith
*Assistant Examiner*—Ginny Allen Portner
(74) *Attorney, Agent, or Firm*—Jacobson Holman, PLLC

(57) ABSTRACT

This invention relates to a method of selecting nonpathogenic bacterial strains capable of binding to the receptor sites for tissue adhesion of pathogenic bacterial strains, comprising the steps consisting in:

Figure 1:
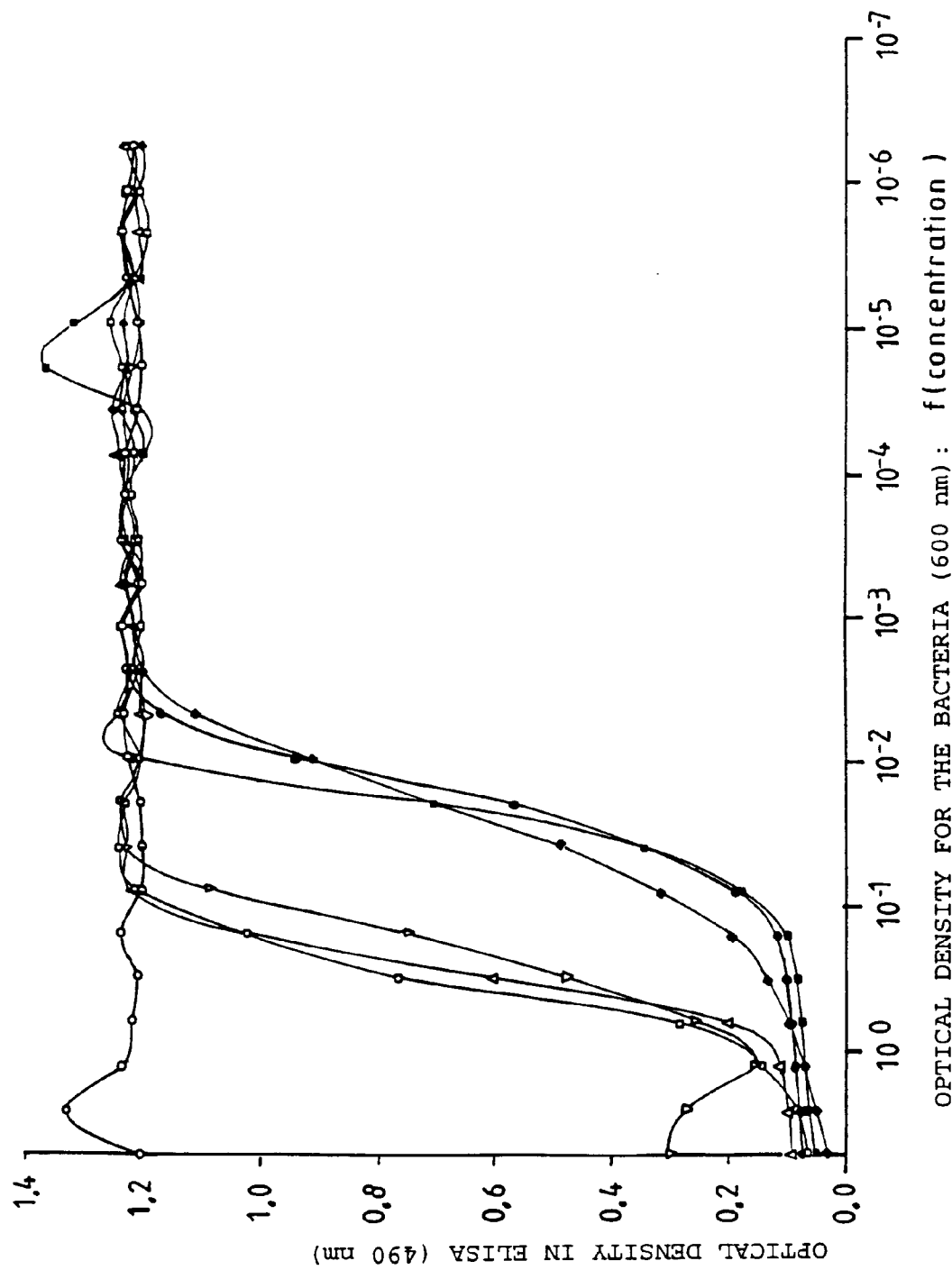

a) bringing the said receptors into contact in vitro with a bacterial strain to be tested;

b) adding an antibody directed against the said receptors, the said antibody being optionally labelled in a detectable manner;

c) in the case where the said antibody is itself not labelled in a detectable manner, adding an agent for detecting the antibody;

d) detecting the presence of the complex formed between the said antibody and the said receptors.

6 Claims, 2 Drawing Sheets

METHOD OF SELECTING BACTERIAL STRAINS

The present invention relates to a method of electing nonpathogenic bacterial strains useful for he prevention or treatment of infections mediated by issue adhesion of pathogenic bacterial strains.

In numerous bacterial infections, it is possible to observe an early phase during which the pathogenic agent adheres to particular sites of the host organism.

This adhesion makes it possible, in particular, for pathogenic bacteria to become established at sites of infection, such as the mucous membranes, which are continually washed by their own secretions and which may be subject to movements such as peristaltism. The adhesion can also help a pathogenic bacterium in its competition with the host's microflora.

The adhesion of a pathogenic bacterium to a tissue is frequently stereospecific and can only take place if the tissue carries a very specific type of receptor. The interaction between a bacterial lectin and a tissue sugar is a typical example of stereospecific interaction. These lectin molecules are often carried by filamentous appendages called fimbriae.

Fimbriae are very fine protein filaments found mainly, and very commonly, in Gram-negative bacteria. They may be distributed over the entire surface of the cell or they may be more localized. A fimbria consists of a repeating linear protein subunit. These subunits are often rich in nonpolar amino acids, such that cells carrying fimbriae tend to have more hydrophobic surfaces than those of cells lacking them. In Gram-negative bacteria, many types of fimbria bring about the adhesion of cells to each other and of cells to any surface. Each type of fimbria indeed possesses its lectin and adheres only to a specific receptor composed of glycoprotein epitopes.

Adhesion through specific types of fimbria is in particular essential for the virulence of enterotoxinogenic *Escherichia coli* strains (ETEC strains). These strains adhere to the duodenal mucosa and produce enterotoxins responsible, for example, for diarrhoeas.

The authors of the present invention have now developed a method for preventing tissue binding of pathogenic bacteria, the said method using nonpathogenic bacterial strains selected for their capacity to bind to the receptor sites for pathogenic bacteria with an affinity superior or equal to the latter.

The present invention relates more particularly to a method of selecting nonpathogenic bacterial strains capable of binding to the receptor sites for tissue adhesion of pathogenic bacterial strains, comprising the steps consisting in:

a) bringing the said receptors into contact in vitro with a bacterial strain to be tested;
  b) adding an antibody directed against the said receptors, the said antibody being optionally labelled in a detectable manner;
  c) in the case where the said antibody is itself not labelled in a detectable manner, adding an agent for detecting the antibody;
  d) detecting the presence of the complex formed between the said antibody and the said isolated receptors.

The detection of the complex formed between the said antibody and the said receptors can therefore be carried out directly, by labelling the said antibody in a detectable manner, or indirectly, by using an agent for detecting the antibody.

The expression "antibody labelled in a detectable manner" is understood to mean that the antibody is conjugated or coupled with a labelling group.

The labelling group may be of various types such as, for example, the radioisotope (such as $^{125}I$, $^{3}H$), enzymatic (in particular by means of alkaline phosphatase, horseradish peroxidase or β-galactosidase), fluorescent, (in particular by means of fluorescein or rhodamine) or particulate (in articular by means of latex or colloidal gold) type. These labelling groups are well known to persons skilled in the art.

The conjugation or coupling of the various markers with the antibody is carried out by conventional methods (coupling with glutaraldehyde, carbodiimide, maleic anhydride, succinic anhydride, heterobifunctional agents and the like).

"Agent for detecting the antibody" designates any means which make it possible to indirectly detect the said antibody. The said detection agent may be in particular a second antibody directed against the said antibody to be detected (or first antibody), the said second antibody being labelled in a detectable manner.

According to the invention, various methods of detection may be used: radioimmunological assay (RIA), immunoenzymatic assay (EIA, ELISA), fluoroimmunological assay (FIA), immunochemiluminescent assay (CLIA), immunoagglutination assay (IA), immunonephelometry, and the like.

The detection of the complex formed between the said first antibody and the said receptor may also be carried out by a Davidoff-type immunocytochemical method which combines the double peroxidase-anti-peroxidase technique with that of the avidin-biotin-peroxidase complex.

According to a preferred embodiment of the method of the invention, the bacterial strain to be tested is brought into contact with the said receptors in a decreasing bacterial concentration. The objective is to search, among various bacterial strains tested, for the one capable of exerting the greatest inhibition of the binding of the antibody to the receptor, for the highest possible dilution of bacteria with reference to the profile for the negative and positive controls.

The antibodies directed against the receptors for tissue adhesion of pathogenic bacteria strains may be mono- or polyclonal antibodies or fragments thereof, chimeric or immunoconjugated antibodies.

Polyclonal antibodies may be obtained from the serum of an animal immunized with the said receptor purified according to the customary procedures.

Preferably, however, monoclonal antibodies are used which may be obtained according to the conventional method of hybridoma culture described by Kohler and Milstein, from preparations of purified receptors for tissue adhesion.

The antibodies may be chimeric antibodies, humanized antibodies, Fab and F(ab')2 fragments. They may also be provided in the form of immunoconjugates or of labelled antibodies.

Among the bacterial strains whose pathogenicity is mediated by tissue adhesion, there may be mentioned in particular the enterotoxinogenic *E. coli* strains, one of the most widespread being the strain identified by its ETEC/0147: K88ac serotype (Erickson et al., Infection and Immunity, 1992, 60:983–988).

The brush-like borders of the enterocytes of sensitive piglets express a receptor which allows massive binding of the strain of this pathogen. The binding of the bacterium is immediately followed by a cascade of intramembrane molecular reactions in the enterocyte which disrupts the ion flows causing a loss of water which, generalized to the whole intestine, finishes by irreversibly dehydrating the piglet to death. In another example, the fimbriae of *E. coli* K99 bind to N-glycolylneuraminyllactosyl ceramides but not to N-acetylated derivatives of sialic acid. The N-glycolyl bonds are in particular present in animals and in particular bovines which are greatly affected by *E. coli* K99.

Among the bacterial strains whose pathogenicity is mediated by tissue adhesion, there may also be mentioned Salmonellae. In these bacteria, the fimbriae are essential for initiating colonization, in particular in the caecum of poultry, a step preceding infection. The adhesion of pili is also essential for *Neisseria gonorrhoeae* to exert its virulence. In addition, the bacteria *Streptococcus mutans, S. sobrinus, S. cricetus* and *S. rattus*, which are the bacteria most frequently encountered in dental caries, are also included. These bacteria exhibit the characteristic feature of converting sucrose to glycans by excreting glycosyltransferases. These enzymes are very important for adhesion because the glycan thus formed binds to the enamel and the gum with food particles and turns out to be a very effective receptor for the lectins carried by these Streptococci. Once bound, the Streptococci multiply and cause dental lesions. In the case of the pathogen *Campylobacter jejuni*, it is lipopolysaccharides which play the role of adhesin allowing binding to the epithelial cells and to the mucus causing a severe diarrhoetic state in humans. *Clostridium difficile* also has to combine with the intestinal mucosa in order to be virulent. *Yersinia enterolytica* as well as *Pseudomonas aeruginosa* exert their pathogenicity after becoming bound through proteins located in the outer membrane playing the role of adhesin. *Helicobacter pylori* is responsible for chronic gastric inflammatory diseases and for gastric and duodenal ulcerations. The adhesion of Helicobacter to the gastric cells through adhesins at the surface of the pathogen which bind to a receptor on the gastric mucosa is essential for triggering the ulceration process.

The method of the present invention is particularly advantageous for selecting the nonpathogenic bacterial strains capable of binding to specific receptors of the intestinal wall to which the enterotoxinogenic *Escherischia coli* strains bind.

A preselection of the bacterial strains to be tested may be advantageously carried out. In the case of the infection by ETEC strains, the strains to be preselected, which may be chosen in particular from the lactobacilli, are tested for their capacity to recognize and to bind to fragments of duodenum and enterocytes isolated from piglets sensitive to colibacillus infections.

In the case of infections with avian Salmonellae, anaerobic bacteria are advantageously tested on tissue fractions of enterocytes isolated from the caecum. In the case of avian *E. coli*, lactobacilli would be advantageous to test on tissue fractions of tracheal cells (case of respiratory colibacilloses) or enterocytes (case of digestive colibacilloses). Finally, lactobacilli and bifidobacteria are advantageous candidates in the case of other pathogens isolated from the digestive or urinary tract of an infected human or animal host organism.

The authors of the present invention have thus selected the strains designated by the references D1, 27S and 30S, which enter into competition with the enterotoxinogenic *E. coli* strains for binding to the fimbriae of the intestinal receptors as described above and which are useful for preventing the expression of the pathogenicity of the said ETEC strains. The 27S and 30S strains were isolated from the small intestine of 6- to 16-week old piglets and were identified as being two lactic acid bacteria which are part of the genus Lactobacillus and of group III of the strict heterofermentative lactobacilli, a species of *Lactobacillus fermentum*. The D1 strain is a lactic acid bacterium which is part of the genus Lactobacillus and of group I of the strict homofermentative lactobacilli, a species of *Lactobacillus salivarius*.

"Host organism" is understood to mean a human or a nonhuman animal which harbours the intended bacterial strains. Among the animals considered as host organisms, there may be mentioned in particular pigs, in particular piglets, cows, in particular calves, as well as sheep, poultry, in particular chicken, and the like.

Piglets are particularly sensitive to the toxins secreted by many strains of enterotoxinogenic colibacilli, in particular after weaning, during the period when they are no longer protected by the antibodies in mother's milk, before their own production of antibodies has become established.

The subject of the present invention is also a method of therapeutic treatment according to which an effective quantity of nonpathogenic bacterial strains selected by the method according to the invention is administered to a human or animal subject requiring such a treatment.

The subject of the present invention is thus a therapeutic composition comprising a bacterial strain selected by the method of the invention, in combination with a pharmaceutically acceptable vehicle.

The pharmaceutical compositions according to the invention may be administered in particular by the oral route.

Their optimum modes of administration, dosages and galenic forms may be determined according to the criteria generally taken into account in establishing a therapeutic treatment suitable for a patient, such as for example the age or body weight of the patient, the seriousness of his general condition, the tolerance to treatment, the side effects observed and the like.

The bacterial strains selected by the method according to the invention may also be administered to animals by incorporating into the drink or the feed, such as in particular force-fed feeds, soups or any other liquid or pasty feed.

The subject of the present invention is also the use of nonpathogenic bacterial strains selected by the method as defined above for the manufacture of a therapeutic composition intended for the prevention or treatment of pathological disorders associated with an infection of a host organism with pathogenic bacterial strains which bind to the said receptors mediating tissue adhesion.

Among the targeted pathological disorders, there may be mentioned in particular those associated with an infection with enterotoxinogenic *Escherischia coli* strains.

The following examples and figure illustrate the invention without limiting it in any manner.

LEGEND TO THE FIGURES

FIG. 1 in the annex represents the result of an ELISA assay on a preparation of intestinal receptor at 10 µg/ml with five bacterial strains, in the presence of an anti-receptor IgM monoclonal antibody (designated by the reference 7E8aB4) (0.24 µg/ml), and of a peroxidase-labelled anti-IgM antibody.

The strains tested are the strains 27S (●), 30S (■), 36S (Δ), LB14 (∛) and D1(♦). A positive control (○) was prepared in the presence of an antibody 7E8aB4 and of a peroxidase-labelled anti-IgM antibody, in the absence of any bacterial strain. A negative control (□) was prepared in the presence of an antibody 7E8aB4 and of a peroxidase-labelled anti-IgM antibody and of strain 3A.

Figure 2:
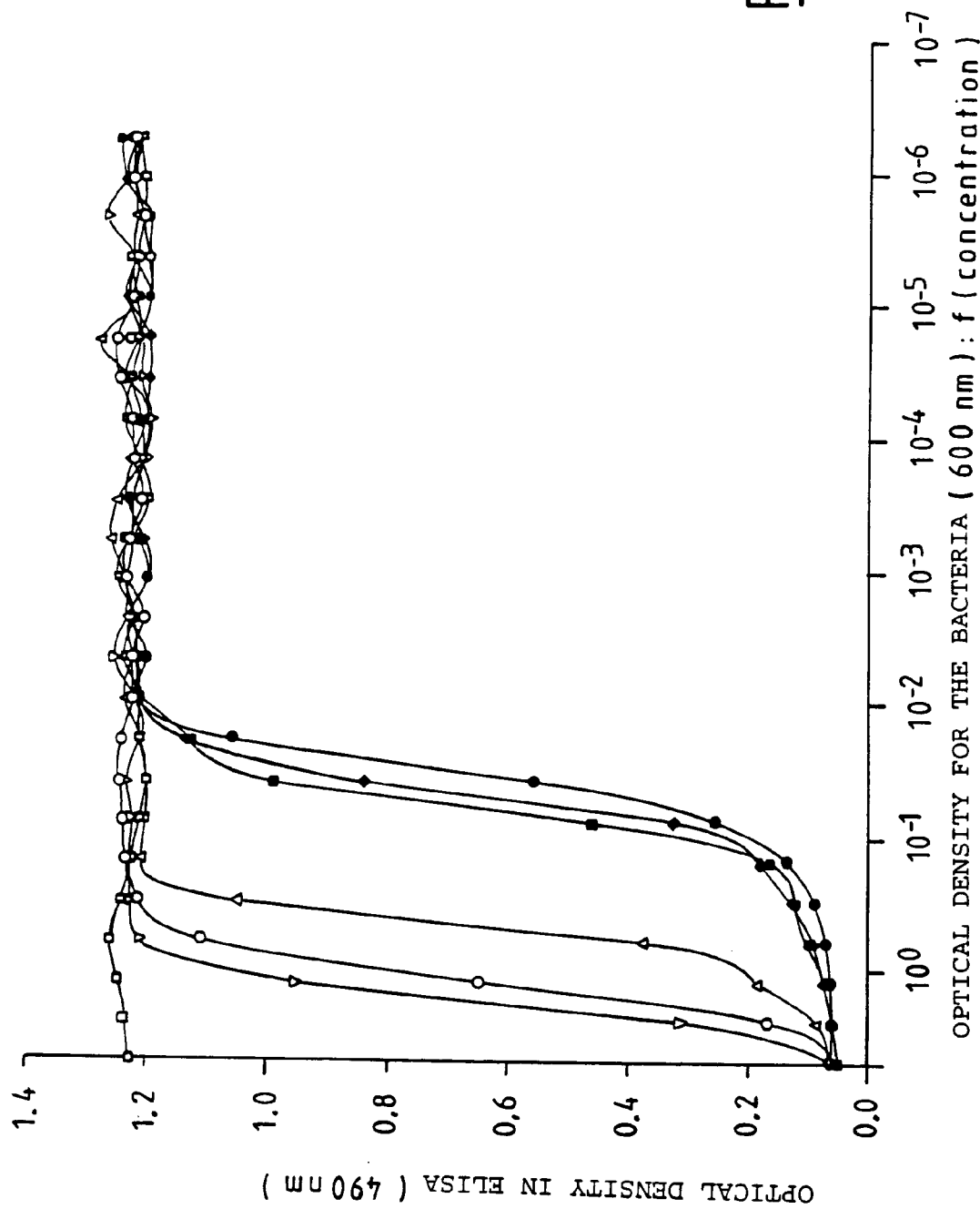

FIG. 2 in the annex represents the result of an ELISA assay on a preparation of intestinal receptor at 10 µg/ml with five bacterial strains, in the presence of purified K88ac fimbriae (12.5 μg/ml), of anti-K88ac serum, biotinylated IgG anti-serum and of the streptavidin-horseradish peroxidase complex.

The strains tested are the strains 27S (●), 30S (■), 36S (Δ), LB14 (▽) and D1(♦). A positive control (○) was prepared in the presence of purified K88ac fimbriae (12.5 μg/ml), of anti-K88ac serum, biotinylated IgG anti-serum and of the streptavidin-horseradish peroxidase complex, in the absence of any bacterial strain. A negative control (□) was prepared in the presence of purified K88ac fimbriae (12.5 μg/ml), of anti-K88ac serum, biotinylated IgG anti-serum, of the streptavidin-horseradish peroxidase complex and of strain 3A.

EXAMPLE

Selection of nonpathogenic bacterial strains capable of binding to the receptor sites for an enterotoxinogenic colibacillus.

I—Purification of the Receptors

Many studies have been undertaken to purify the receptor (Cohen et al., Fractionation and characterization of mouse small intestine mucus and brush border receptors for the K88ab adhesin, Microecology and Therapy, 1985, 15: 71–83 and Erickson et al., Infection and Immunity, 1992, 60: 983–988). The whole difficulty lies in obtaining a sufficient yield of active receptors to start the production of monoclonal antibodies.

Piglets sensitive to experimental colibacilloses, and therefore expressing receptors for colibacilli, were selected and separated from resistant animals lacking receptors (Valpotic I et al., Veterinarski Arhiv, 1989, 59: 161–175 and Valpotic I. et al., Periodicum Biologorum, 1990, 92: 43–44). The mucous membrane of the small intestine was then carefully removed and homogenized in the presence of protease inhibitors. The vesicles of the brush border of the enterocytes were separated from the components of the mucus and then the highly glycosylated receptors were extracted from the vesicles by ultrasonic treatment and by the combination of alcohol and phenol precipitations. The aqueous phase enriched with receptors was finally dialysed and then lyophilized. After each purification step, the receptor was tested by Western blotting for its capacity to bind the fimbriae of the bacterium K88ac.

The detailed purification protocol is the following:

The purification of the receptor starts with the production of the brush border vesicles.

In this first step, the intestinal mucosa is carefully removed from a 10-cm intestinal segment and then deposited in a Potter. A volume of buffer equal to five times the mass of mucosa and consisting of 50 mM mannitol, 2 mM Tris-HCl of pH 7.4, and protease inhibitors [PMSF (phenylmethylsulphonyl fluoride), trypsin inhibitor, Pepstatin A and Leupeptin] is added to the Potter. The suspension is then ground by 15 reciprocating movements of the piston. A volume of the same buffer equal to five times the volume of the suspension is then added. The suspension is again ground by fifteen reciprocating movements of the piston. The volume of the solution estimated between 7.5 and 17.5 ml is then brought into contact for 20 minutes at 0° C. with a solution of $MgCl_2$ in order to reach a percentage of 1%. Two centrifugations of 3000 and 27,000 g for fifteen to thirty minutes respectively are carried out in order to recover the pellet resolubilized in 100 μl of buffer. The protein concentration is then determined.

The receptors are then extracted from the brush border vesicles so as to be semipurified.

In this second step, CHAPS, 3-[(3-cholamido-propyl) dimethylammonio]-1-propanedsulphonate, detergent corresponding to five times the quantity of protein is added to the 100 μl of suspension. The proteins are solubilized in a Potter by 15 reciprocating movements of the piston. The solubilization is continued for twelve hours at 4° C. The solution is then centrifuged at 125,000 g for one hour. The supernatant is removed, dialysed for 24 hours at 4° C. (MWCO: Molecular Weight Cut-Off 12,000–14,000) and centrifuged for one hour at 125,000 g. The supernatant is taken up so as to be dialysed and centrifuged again as above twice in succession. After each centrifugation, the pellet is resolubilized in distilled water. The final volume of solution does not exceed 1 ml.

The semipurified receptors are then treated in order to obtain purified receptors.

In this third step, the preparation is first subjected to ultrasound (15 watts) for three times 15 seconds in melting ice. It is then centrifuged at 125,000 g for 40 minutes. The pellet is again resolubilized in 1 ml of distilled water and the ultrasound treatment is again carried out. This operation is repeated twelve times. After each centrifugation step, the supernatant is deposited in a tube in contact with melting ice. The entire supernatant is concentrated in a dialysis tube (MWCO: 10,000) against solid PEG until one third of the initial volume is obtained. The concentrated preparation is then diluted in ethanol by adjusting the preparation to 11% alcohol and then it is incubated for twenty minutes in melting ice. The preparation is then centrifuged at 125,000 g for forty minutes. The purity of the pellet in terms of receptors is estimated by SDS-PAGE electrophoretic analysis. The receptors are treated successively in the same manner as above but in solutions of ethanol at 20, 33, 43, 55 and 64%. The receptors are collected from alcoholic precipitations at 43, 55 and 64%. They are solubilized in distilled water and then lyophilized.

II—The Production of Monoclonal Antibodies Specific for the Receptors

The production of monoclonal antibodies specific for the receptors was carried out according to a method derived from Köhler and Milstein (Nature, 1975, vol. 256, pp 49–497).

The receptors purified according to the method described above were injected into Balb/c albino mice. Testing for the best serum antibody titres made it possible to select three mice chosen for three cell fusions. The fusion consisted in collecting, from the spleen of the mouse, antibody-secreting B lymphocytes and to fuse these cells with cancerous lymphoblastic cells. The selective growth of the hybridomas in culture was brought about by the set of inhibitors of DNA synthesis and the activity of the anti-receptor antibodies in the culture supernatants was tested.

The following experiments consisted in isolating the cells in an amount of one hybrid cell per well. Each supernatant of each of the wells containing cells which are all identical is assayed by ELISA to test for the best anti-receptor activity. The clones of interest were then injected into mice conditioned with pristane for the massive production of antibodies in ascitic fluid, which were finally purified and characterized (J. H. Peters et al., Monoclonal antibodies, 1992, 475 and L. Hudson et al., Practical Immunology, 1989: 496).

III—Validation of the Monoclonal Antibodies

Using the clones obtained, 20 antibodies were tested by three techniques (immunocytochemistry, ELISA and BIAcore) for their capacity to recognize the intestinal receptor. Six antibodies were selected. These antibodies were then analysed by ELISA and BIAcore for their capacity to inhibit the binding of the fimbriae of K88ac to their receptor by molecular competition. Two antibodies inhibited the binding of the bacterial adhesins 100% and were chosen as immunological tools in the selection test below. One of the monoclonal antibodies produced is identified by the reference 7E8aB4.

IV—Selection of Bacterial Strains

The strains tested were collected from pigs in slaughterhouses. These strains belong to the genera and species *Lactobacillus fermentum, L. delbrueckii, L. acidophilus, L. salivarius, Leuconostoc lactis*, this list not being exhaustive. These strains have been the subject of preliminary tests to verify their capacity for adhesion to the intestinal mucosa, and to the isolated enterocytes.

a) Description of the protocol

| Composition of the MRS medium: | |
| --- | --- |
| Proteose Bacto-peptone No. 3 | 10 g |
| Bacto-beef extract | 10 g |
| Bacto-yeast extract | 5 g |
| Bacto-dextrose | 20 g |
| Tween 80 | 1 g |
| Ammonium citrate | 2 g |
| Sodium acetate | 5 g |
| Magnesium sulphate | 0.1 g |
| Manganese sulphate | 0.005 g |
| Dipotasium phosphate | 2 g |

Resuspension of 55 g of powder in 1 litre of water:
Final pH 6.5+0.2 at 25° C.

A preliminary culture of the bacterial strain to be tested is essential before carrying out the test. The bacteria are cultured in liquid MRS medium at 37° C. under microaerophilic conditions. They are then separated from the supernatant by centrifugation and resuspended in phosphate buffered saline (PBS), (pH 7.3). The solution of bacteria is adjusted to an optical density (OD) of 5 (OD of 0.5 at 600 nm=$3 \times 10^8$ bacteria per ml) and then diluted ½ twenty-four times. The pure supernatant is diluted ½ twelve times.

This test consists in adsorbing the intestinal receptor in the microwells of ELISA plates overnight at 4° C. in phosphate buffered saline. The spaces between the receptors are filled with a saturating agent (BSA at 1%) for 30 minutes at room temperature. After three washing steps, 50 µl of each of the solutions of the range of bacterial strains (or of culture supernatant) are deposited successively in 24 or 12 wells respectively. After 12 hours of incubation at 4° C. or 2 hours of incubation at 37° C., 50 µl of monoclonal antibody 7E8aB4 of constant concentration at 0.24 µg/ml are added to all the wells. The antibody concentration was previously adjusted in order to obtain a satisfactory signal of the order of OD=1.2 in ELISA. A series of three washes is again carried out, and the rest of the test consists in detecting the presence of 7E8aB4 in the wells using peroxidase-conjugated antibodies which are capable of recognizing 7E8aB4. A substrate of the enzyme (O-phenylenediamine) is distributed in all the wells of the ELISA plate. Thus, if the antibody-receptor conjugate is present in a well, the enzyme degrades the substrate, developing a localized coloured reaction whose intensity is directly dependent on the quantity of antibody present. The optical density values in each well are determined precisely by an ELISA plate reader.

b) Results

The optical density values are compared with those for the positive controls (in the presence of 7E8aB4 antibody only). A constant monoclonal antibody concentration gives a constant coloured signal, and therefore an OD value close to 1.2. If the bacteria tested are capable of preventing the binding of the antibody, the OD values should drop significantly in correlation with the number of bacteria present. The curves obtained are different depending on the strains tested. The profile of the curves is analysed and compared with that of a negative control represented by a reference strain known for its lack of adhesion (strain No. 3A of the accompanying FIG. 1). This negative control also makes it possible to differentiate a specific inhibition from a nonspecific inhibition of the binding of the antibody. The nonspecific inhibitions are caused by hindrance by bacterial bodies for high concentrations of microorganisms. The objective is to search for the bacteria capable of exerting the greatest inhibition (lowest OD) for the highest possible dilution of microorganisms with reference to the profile of the negative and positive controls.

When the profile obtained with a strain is almost superimposable with that of the negative control, and when furthermore the OD value increases very rapidly from the first dilutions to reach the plateau for the maximum OD set at the value of 1.2, it can be concluded that this strain does not prevent the binding of the antibody to the receptors (strain No. 36S of the accompanying FIG. 1). On the other hand, compared with the control, some strains exert a prolonged inhibitory activity for low concentrations of bacteria (example of strains Nos. D1, 27S and 30S in the accompanying FIG. 1). The curves obtained can be easily differentiated from those for the nonadherent control strains because they are shifted to the right in the accompanying figure (direction of the low concentrations of bacteria). The more the curves are shifted to the right, the more the bacterial strains are of interest and effective for being in competition with the ETEC strains on the site of adhesion of fimbriae of K88ac.

Strains Nos. 36S and LB14:

Strain 36S was isolated from the colon of a 6-week old piglet and was identified as being a lactic acid bacterium forming part of the genus Lactobacillus and of group I of the strict homofermentative lactobacilli, Lactobacillus belonging to the first complex, a species of *Lactobacillus delbrueckii*, a subspecies to be determined by fine analysis by PCR.

Strain LB14 was freshly isolated from the duodenum of 6-week old piglets. It is a lactic acid bacterium forming part of the genus Lactobacillus and of group II of the facultative heterofermentative lactobacilli, Lactobacillus belonging to the second complex, a species of *Lactobacillus casei*, a subspecies to be determined by fine analysis.

For strains 36S and LB14, as soon as the dilution of bacteria increases, the optical density values also increase very rapidly, following the profile of the negative control and reaching the optimum density for low dilutions of nonpathogenic bacteria. The inhibition observed is essentially caused by a very large number of bacteria in the wells of the ELISA plates, thereby preventing access of the antibody to its receptor bound to the bottom of the wells. In the context of such a nonspecific cellular hindrance, a 50% inhibition (OD of 0.4) is close to a load of $12 \times 10^6$ bacteria/well. It may be considered that trains attributing similar results are not of interest or undertaking an in vivo challenge test.

Strains 30S (*L. fermentum*) and 27S (*L. fermentum*):

Strains 27S and 30S were isolated from the small intestine of 6- to 16-week old pigs and were identified as being two lactic acid bacteria forming part of the genus Lactobacillus and of group III of the strict heterofermentative lactobacilli, a species of *Lactobacillus fermentum*.

In these examples, a very marked difference is observed with the profile of the strains which is described above. Indeed, in spite of several ½ dilutions of the nonpathogenic bacteria, the inhibition persists because the optical density values remain stable and close to the base line. The first phases of the inhibition are caused by a nonspecific bacterial hindrance but are then extended by a more specific inhibition on the receptor site of our immunological tool. A higher dilution of nonpathogenic bacteria than that of the negative control is required in order to observe the gradual lifting of the inhibition. For 50% inhibition (OD of 0.02), the bacterial load in the well is of the order of $60 \times 10^4$, that is 20 times less concentrated than the bacterial load of the negative control and of strains 36S and LB14. These strains are selected in order to continue experimental tests in vivo.

Strain D1:

Strain D1 is a lactic acid bacterium forming part of the genus Lactobacillus and of group I of the strict homofermentative lactobacilli, a species of *Lactobacillus salivarius*.

Despite the fact that the inhibition is lifted earlier than that of strains 27S and 30S, it is however, slightly more long-lasting. Consequently, for 50% inhibition (OD of 0.03), the nonpathogenic bacterial load in the well is of the order of $90 \times 10^4$, that is 1.5 times more concentrated than that for strains 27S and 30S but remains all the same 13 times less concentrated than the bacterial load of the negative control and of strains 36S and LB14. This intermediate inhibition profile is therefore close to that for the strains selected. Strain D1 is therefore a good candidate for the in vivo competition tests.

The present invention therefore makes it possible to select nonpathogenic bacterial strains capable of specifically preventing the binding of enterotoxinogenic bacteria and therefore the expression of their pathogenicity. The preventive administration of the nonpathogenic strains selected makes it possible to avoid the appearance of disorders caused by an infection by enterotoxinogenic bacteria, such as diarrhoea. Their administration for curative purposes makes it possible to attenuate or even eliminate these same disorders.

V—Confirmation In Vitro of the Inhibitory Capacities of Strains Selected a) Materials and Methods In order to evaluate the inhibitory capacities of the culture supernatants and of washed bacteria towards the antibody, a control test was undertaken by replacing the antibody with purified fimbriae of K88ac. In this case, an anti-K88ac polyclonal serum and anti-serum conjugated antibodies are used for the detection of the presence of fimbriae.

In this test, the intestinal receptor is deposited in the microwells of ELISA plates and then left overnight at 4° C. in phosphate-buffered saline. The spaces between the receptors are filled with a saturating agent (bovine serum albumin BSA at 1%) for 30 minutes at room temperature. After three washing steps, 50 $\mu$l of each of the solutions of the range of strains previously selected (or of culture supernatant) are deposited successively in 24 or 12 wells respectively. After twelve hours of incubation at 4° C. or two hours of incubation at 37° C., 50 $\mu$g of preparation of K88ac fimbriae having a constant concentration at 12.5 $\mu$g/ml are added to all the wells. The concentration of fimbriae was previously adjusted in order to obtain a satisfactory signal of the order of OD=1.2 by ELISA. A series of three washes is again carried out and the rest of the test consists in detecting the presence of the K88ac fimbriae in the wells using polyclonal antibodies obtained from a rabbit antiserum. The rabbit antibodies which recognized the fimbriae are themselves detected after washing with biotin-conjugated antibodies. An enzymatic complex (streptavidin/horseradish peroxidase) capable of recognizing the biotin is then added. Finally, a substrate of the enzyme (O-phenylenediamine) is distributed in all the wells of the ELISA plates for the development of the coloured reaction. These cascades of recognition are necessary because the K88ac fimbriae are very hydrophobic and the use of an excessively high concentration of fimbriae can cause the appearance of nonspecific bindings of the bacterial lectins. One molecule of streptavidin complex carries several peroxidase enzymes. Thus, the use of these enzymatic complexes makes it possible to work with low concentrations of fimbriae while amplifying the colour signal.

b) Results

The optical density values were compared with those of controls containing only the K88ac fimbriae on the receptor (FIG. 2). A constant concentration of fimbriae gave a constant coloured signal and therefore an OD value of close to 1.2. According to the results, the binding of the fimbriae is more difficult to inhibit than that of the 7E8aB4 antibody. Indeed, more bacteria are necessary per well in order to observe an inhibition of fimbriae comparable to that of the test using the monoclonal antibody. This difference may be explained by a difference between the number of binding sites for the antibody used and for the fimbriae. A molecule of IgM carries ten recognition sites whereas a fimbria certainly carries a lot more. However, despite this difference, the classification of the strains selected according to their inhibitory activity does not change.

VI—Validation In Vivo of the Efficacy of the Strains Selected

The process described above results in the selection of nonpathogenic bacterial strains which bind specifically to the receptors for the fimbriae of *E. coli* K88ac of the intestinal mucosa of piglets. It is then necessary to validate in vivo this binding by virtue of which the bacterial strain selected can multiply in the small intestine and ensure an effective prevention against the binding of *E. coli* K88ac.

To this effect, piglets are kept on the side from birth and placed in isolating devices before ingestion of colostrum. They receive conventional liquid feed. As a result, these piglets do not lack microbial flora, but do not have the benefit of the immune protection offered by the colostrum.

These piglets receive in their diet a nonpathogenic bacterial strain as selected above for three days. They are then administered a dose of $5 \times 10^8$ CFU of a toxicogenic *E. coli* K88ac strain. The piglets are humanely killed 24 hours after this administration, and the concentration of total microorganisms, of *E. coli* and of the nonpathogenic bacterial strain selected are measured in the various segments of the small intestine such as the caecum. Moreover, the genetic sensitivity of these piglets to *E. coli* K88ac is determined.

If the piglets which are sensitive, and therefore carrying adhesion sites, have a significantly higher concentration of the nonpathogenic bacterial strain selected than the resistant piglets, this means that this strain has been able to bind to the adhesion sites and multiply. This bacterial strain will therefore be capable of modifying the microbial flora of the small intestine in a direction which is unfavourable to *E. coli* K88ac.

What is claimed is:

1. A method for screening nonpathogenic bacterial strains for their ability to bind to host tissue receptor sites specific for pathogenic bacterial strains whose pathogenicity to the animal is mediated by tissue adhesion, said method comprising the steps of:

a) bringing the host tissue receptor sites into contact in vitro with a nonpathogenic bacterial strain;

b) adding an antibody directed against the receptor sites;

c) labeling the antibody in a detectable manner, before or after the step of adding the antibody; and d) detecting for the presence of a complex formed between the antibody and the receptor sites; whereby, the fewer of said complexes detected compared with a total antibody binding control, the greater the ability of said nonpathogenic bacterial strain to bind to said host receptor sites.

2. Method according to claim 1 in which the antibody is labeled by a second antibody directed against the antibody, the second antibody being labeled in a detectable manner.

3. Method according to claim 1, in which the receptor sites are specific receptors of the intestinal wall to which enterotoxinogenic *Escherichia coli* strains bind.

4. Method according to claim 2, in which the receptor sites are specific receptors of the intestinal wall to which enterotoxinogenic *Escherichia coli* strains bind.

5. The method according to claim 1, wherein the antibody directed against the tissue receptor sites is a first antibody, wherein labeling the antibody is performed after the step of adding the first antibody by adding a detection agent comprising a second antibody labeled in a detectable manner and directed against said first antibody.

6. The method according to claim 5, wherein the tissue receptor sites are intestinal wall receptors specific for pathogenic enterotoxinogenic *Escherichia coli* strains.

* * * * *